(12) United States Patent
Taylor

(10) Patent No.: US 6,916,495 B2
(45) Date of Patent: Jul. 12, 2005

(54) PREPARATION FOR REGULATING LOWER BOWEL FUNCTION

(76) Inventor: Allan Taylor, 16 Halyard Walk Eastlake Island, Marina de Gama, 7945, Western Cape (ZA)

( * ) Notice: Subject to any disclaimer, the term of this patent is extended or adjusted under 35 U.S.C. 154(b) by 0 days.

(21) Appl. No.: 10/420,524

(22) Filed: Apr. 22, 2003

(65) Prior Publication Data

US 2004/0009246 A1 Jan. 15, 2004

Related U.S. Application Data

(63) Continuation of application No. 09/939,427, filed as application No. PCT/ZA00/00029 on Feb. 23, 2000, now abandoned.

(30) Foreign Application Priority Data

Feb. 24, 1999 (ZA) .............................................. 99/1462
Mar. 8, 1999 (ZA) .............................................. 99/1821

(51) Int. Cl.[7] .............................................. A61K 35/78
(52) U.S. Cl. ...................................... 424/744; 514/867
(58) Field of Search ........................... 424/744; 514/867

(56) References Cited

U.S. PATENT DOCUMENTS

| | | | | |
|---|---|---|---|---|
| 4,917,890 A | * | 4/1990 | McAnalley | 424/744 |
| 4,927,624 A | * | 5/1990 | Bryant et al. | 424/9.31 |
| 5,140,949 A | * | 8/1992 | Chu et al. | 119/174 |
| 5,165,915 A | * | 11/1992 | Tokubo et al. | 424/63 |
| 5,380,522 A | * | 1/1995 | Day | 424/78.08 |
| 5,618,527 A | * | 4/1997 | Mendes et al. | 424/78.01 |
| 5,929,051 A | * | 7/1999 | Ni et al. | 514/54 |
| 5,977,175 A | * | 11/1999 | Lin | 514/558 |
| 6,503,517 B1 | * | 1/2003 | Mohammadi et al. | 424/401 |
| 2001/0041718 A1 | | 11/2001 | Thompson et al. | |

FOREIGN PATENT DOCUMENTS

| | | |
|---|---|---|
| DE | 3627010 | 2/1988 |
| EP | 256353 | 2/1988 |
| JP | 63044530 | 2/1988 |
| JP | 2001097883 A * | 4/2001 |

OTHER PUBLICATIONS

Product Alert, "Naturade Colon Conditioner–Orange Flavored Powder", Jun. 6, 1994, vol. 23, No. 23.*

Product Alert, "Naturade Colon Conditioner–Orange Flavored Powder", Jun. 6, 1994, vol. 23, No. 23.

* cited by examiner

Primary Examiner—Christopher R. Tate
(74) Attorney, Agent, or Firm—Richard S. Vermut; Rogers Towers, P.A.

(57) ABSTRACT

A preparation is described which is intended for regulation of lower bowel function. It comprises a mixture of bentonite and/or kaolin and aloe fibers. The aloe fibres are reduced to a dry powder before being mixed with the bentonite and/or kaolin.

10 Claims, No Drawings

PREPARATION FOR REGULATING LOWER BOWEL FUNCTION

This application is a continuation of application Ser. No. 09/939,427, filed Nov. 27, 2001, now abandoned which is a 371 of PCT/ZA00/00029, filed Feb. 23, 2000.

This application claims the benefit of U.S. application Ser. No. 09/939,427 filed on Nov. 27, 2001, Republic of South Africa patent application number 99/1462 filed on Feb. 24, 1999, Republic of South Africa patent application number 99/1821 filed on Mar. 8, 1999, and PCT application Ser. No. PCT/ZA00/00029 filed on Feb. 23, 2000, each of which is incorporated herein by this reference in its entirety.

FIELD OF THE INVENTION

THIS INVENTION relates to a preparation for regulating lower bowel function.

BACKGROUND TO THE INVENTION

In irritable bowel syndrome (I.B.S.) the mechanical function of the colon is disrupted. The patient classically suffers from alternate bouts of constipation and diarrhea. Flatulence, cramping and pain are also common features of this syndrome.

The consistency of the colon content is very important for normal peristaltic and mechanical movement resulting in voiding to produce a normal bowel movement with faeces the consistency of soft clay. Bowel content that is either too watery or too solid results in disruption of the colon structure, often resulting in disease conditions such as diverticulitis and ulcerative colitis.

The movement of the bowel content through the colon is facilitated by mucous which is secreted by the cells lining the lumen of the colon. If the consistency of the faecal mass is inappropriate, this lubrication effect is lost.

The proliferation of micro organisms in the colon is determined by many factors, such as the amount of undigested food which reaches the colon, the pH, the transit time, faecal consistency etc. Excessive bacterial or fungal activity in the colon is termed putrification and is undesirable as it can lead to bowel disease.

Many products have been formulated to treat I.B.S. However, it has been found that, in extended studies, none are more effective than a placebo.

End stage AIDS patients suffer from diarrhea. Typically the patient at this stage of the disease will have uncontrollable diarrhea. The transit time of meals through the gastrointestinal tract is too rapid to allow sufficient time for digestion and absorption of the nutrients in the food. The patient then loses weight, becomes very thin and eventually dies.

BRIEF DESCRIPTION OF THE INVENTION

According to the present invention there is provided a preparation for regulating lower bowel function which comprises a mixture of bentonite and/or kaolin and Aloe fibres which have been reduced to the form of a dry powder.

The proportion of dry Aloe powder in the preparation can range from 10% to 90% by weight and the proportion of bentonite and/or kaolin from 90% to 10% by weight.

It is preferred that the proportion of fibre powder in the preparation be between 30% and 70% and that the balance be bentonite and/or kaolin.

In the form which Applicants have found to be most effective the fibre powder constitutes 60% by weight and the balance is bentonite and/or kaolin.

Bentonite is the preferred clay as it has medicinal properties. It is best described as a native (natural) colloidal hydrated aluminum silicate of montmorillite $Al_2O_3$, $4siO_2$, $H_2O$ with trace quantities of other minerals such as magnesium and iron with some calcium carbonate. In water bentonite swells to form a colloidal gel.

The powder is preferably produced from the leaves of the Aloe Ferox plant. However, Aloe Vera or any other type of Aloe which is plentiful and robust enough to withstand sustainable harvesting can be used. Aloe Ferox is a natural dietary fibre prepared from leaves of Aloe Ferox, an abundant species growing wild in its natural habitat in the Southern Cape region of South Africa. The leaves of this species have been harvested by traditional aloe tappers for the production of crystalline Aloe Bitters, which has been exported to Europe and the East since 1763. The traditional manner of collecting the aloin-containing bitter sap and converting it to hard crystals continues on a sustainable basis and does not present any threat to the environment.

For the production of Aloe Ferox powder, leaves already cut by the tappers and from which the bitter sap has drained, are collected from the veld, washed and then sliced very thin. Any remaining bitter sap is removed by agitation in warm water (70° C.). Finally the slices are dried in the sun and milled into a fine power. Ferox does not contain any additives. It is derived from plants that have not been artificially fertilized or sprayed with insecticides or fungicides. The only natural constituents removed from the leaves in the production process are aloin and its derivatives, as well as resins, in the bitter sap.

The Composition of Aloe Ferox per 100 g. of leaf powder, and its characteristics, are as follows:

| | |
|---|---|
| Total dietary fibre | 43.0 g |
| Insoluble fibre | 28.7 g |
| hemi-cellulosic polymers, mainly xylans | |
| cellulose | |
| lignin | |
| Soluble fibre | 14.3 g |
| pectin polymers | |
| arabinogalactan | |
| rhamnogalacturonan | |
| Water hydration capacity | |
| Approximately seven times its own weight. | |
| Viscosity | 260 cps. At 20° c. |

Viscosity is measured as a 3% suspension of leaf powder after heating in 2% potassium citrate solution to sequestrate the polysaccharide gel from the leaf calcium.

| | |
|---|---|
| Aloin and derivatives | Absent |
| This is shown by a negative Borntraeger reaction | |
| Microbial count | CFU/g |
| Total microbial activity | 710 |
| Pathogens | absent |
| Moulds | 50 |
| Analysis of Particle size | Sieve analysis |
| >500 microns | 1.5% m/m |
| 500–125 microns | 62.8% m/m |
| 125–45 microns | 30.7% m/m |
| <45 microns | 5.0% m/m |
| Mineral content per 100 g. of leaf powder | |
| Calcium | 4.08 g |
| Potassium | 0.08 g |
| Sodium | 0.18 g |

-continued

| | |
|---|---|
| Magnesium | 0.44 g |
| Iron | 34.0 mg |
| Copper | 9.5 mg |
| Manganese | 4.8 mg |
| Zinc | 3.1 mg |
| Boron | 2.5 mg |
| Selenium | 6.3 ppm |
| Ash | 11.8 g/100 g |
| Moisture | 10.2 g/100 g |
| Carbohydrates (calculated) | |
| 50.0 g/100 g (glyco-proteins (mainly pectic polymers) | |
| Amino acids as g. per 100 g leaf powder | |
| Aspartic acid | 0.03 |
| Glutamic acid | 0.07 |
| Serine | 0.08 |
| Glycine | 0.11 |
| Histidine | 0.02 |
| Arginine | 0.06 |
| Threonine | 0.11 |
| Alanine | 0.14 |
| Proline | 0.11 |
| Tyrosine | 0.06 |
| Valine | 0.11 |
| Methionie | 0.02 |
| Cysteine | 0.02 |
| Isoleucine | 0.09 |
| Leucine | 0.16 |
| Phenylalanine | 0.10 |
| Lysine | 0.08 |
| Trypotophane | not detected |

DETAILED DESCRIPTION OF THE INVENTION

The invention will now be described in detail with reference to the following example.

Two parts by weight of Aloe Ferox leaf powder was mixed with one part by weight of bentonite. A 3% suspension of the leaf powder in water has a pH of 4.9. A similar suspension of bentonite has a pH of 9.5. A 3% solution of the mixture as described has a pH of 5.2. Bentonite in water absorbs twelve times its own weight. Dry Aloe Ferox powder can absorb up to seven times its own weight.

Experimental work has shown that 10 grams of the Aloe Ferox/bentonite mixture absorbs water and swells, eventually achieving a mass of about 100 grams.

Kaolin, also called china clay, has properties which make it usable as a product for the treatment of humans. It can completely, or partly, replace the bentonite in the product of the present invention.

The product can be formulated as tablets or preferably granules for ease of consumption.

The following are case histories of patients on whom the product has been tested.

Patient 1

This 30 year old female was diagnosed with Irritable Bowel Syndrome five years ago at a state hospital. Her symptoms before treatment were diarrhea with cramping and pain, occasional constipation for which she took irritant laxatives which started the diarrhea phase again. She was thoroughly depressed about her condition, which included gastric hyperacidity. She reported five days after starting treatment with the bentonite/Aloe Ferox powder that her lower bowel function had improved dramatically. She reported a significant improvement in the lower bowel function, with the production of normal stools three times daily.

Patient 2

This 36 year old female was diagnosed with I.B.S. three years previously by a private general practitioner. Her symptoms were lower abdominal pain and discomfort, cramping, constipation with resultant nausea and malaise. She reported that after four days of treatment with the Aloe Ferox/bentonite mixture there was a significant improvement in lower abdominal symptoms, a normal regular daily bowel movement resulted and the patient reported a feeling of satisfaction and well being last experienced prior to the onset of her I.B.S.

Patient 3

This 29 year old female has suffered from mild to moderate I.B.S. for the last eight years, the most common symptom being constipation. She was diagnosed as suffering from I.B.S. by a general practitioner. She reported a significant improvement in her condition after one week of treatment with the Aloe Ferox/bentonite powder. Chronic treatment is not indicated as the constipation occurs sporadically and, when it does, the treatment is taken.

Patient 4

This 38 year old female had chronic constipation for more than one year. She consulted a medical practitioner who prescribed a dietary fibre product. She started using the Aloe Ferox/bentonite powder and reported an almost instant significant improvement.

Patient 5

A 30 year old male Zambian with AIDS was having an average of five bowel movements of a very watery consistency daily when treatment with the powder was initiated. Within days his bowel movements reduced to two a day and a consistency was normal. His general condition improved and after three weeks he had gained two kilograms in weight. The product was administered in powder form at the dosage of one tablespoon three times daily.

All patients have reported a sustained improvement in bowel function for a period of at least three months.

What is claimed is:

1. A preparation for regulating lower bowel function which comprises aloe leaf fibres in the form of a dry aloe powder and bentonite and/or kaolin, the dry aloe powder constituting between 10% and 90% by weight percent of the preparation and the bentonite and/or kaolin constituting between 90% and 10% by weight percent of the preparation.

2. A preparation as claimed in claim 1, wherein the dry aloe powder constitutes between 30% and 70% by weight percent of the preparation and the bentonite and/or kaolin between 70% and 30% by weight percent of the preparation.

3. A preparation as claimed in claim 1, wherein the dry aloe powder constitutes 60% by weight percent of the preparation and the bentonite and/or kaolin constitutes 40% by weight percent of the preparation.

4. A preparation for regulating lower bowel function consisting essentially of leaf aloe fibres in the form of a dry aloe powder and bentonite and/or kaolin, the dry aloe powder constituting between 10% and 90% by weight percent of the preparation and the bentonite and/or kaolin constituting between 90% and 10% by weight of the preparation.

5. A preparation as claimed in claim 4, wherein the dry aloe powder constitutes between 30% and 70% by weight percent of the preparation and the bentonite and/or kaolin between 70% and 30% by weight percent of the preparation.

6. A preparation as claimed in claim 4, wherein the dry aloe powder constitutes 60% by weight percent of the preparation and the bentonite and/or kaolin constitutes 40% by weight percent of the preparation.

7. A method of reducing free water content in the lower bowel which comprises a subject in need thereof ingesting therapeutically effective amounts of a preparation comprising leaf aloe fibres in the form of a dry aloe powder and bentonite and/or kaolin, the dry aloe powder constituting between 10% and 90% by weight percent of the preparation and the bentonite and/or kaolin constituting between 90% and 10% by weight percent of the preparation.

8. The method of claim 7, wherein the dry aloe powder constitutes between 30% and 70% by weight percent of the preparation and the bentonite and/or kaolin between 70% and 30% by weight percent of the preparation.

9. The method of claim 7, wherein the dry aloe powder constitutes 60% by weight percent of the preparation and the bentonite and/or kaolin constitutes 40% by weight percent of the preparation.

10. The method of claim 7, wherein the dry aloe powder and bentonite and/or kaolin are ingested at the dosage of one tablespoon three times daily.

* * * * *